(12) United States Patent
Rucker

(10) Patent No.: US 8,206,433 B2
(45) Date of Patent: Jun. 26, 2012

(54) REMOVABLE COILED STENT

(75) Inventor: Brian K. Rucker, King, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 504 days.

(21) Appl. No.: 11/365,712

(22) Filed: Feb. 28, 2006

(65) Prior Publication Data

US 2006/0224235 A1    Oct. 5, 2006

Related U.S. Application Data

(60) Provisional application No. 60/657,544, filed on Feb. 28, 2005.

(51) Int. Cl.
*A61F 2/06* (2006.01)

(52) U.S. Cl. .............. 623/1.21; 623/1.11; 623/1.15

(58) Field of Classification Search .......... 623/1.11, 623/1.12, 1.14, 1.15, 1.22, 1.33, 23.65–23.67, 623/23.7; 606/191–200
See application file for complete search history.

(56) References Cited

U.S. PATENT DOCUMENTS

| | | |
|---|---|---|
| 4,740,207 A | 4/1988 | Kreamer |
| 5,192,307 A | 3/1993 | Wall et al. |
| 5,618,299 A | 4/1997 | Khosravi et al. |
| 5,961,545 A * | 10/1999 | Lentz et al. .......... 623/1.39 |

FOREIGN PATENT DOCUMENTS

| | | |
|---|---|---|
| EP | 0 246 998 A2 | 11/1987 |
| FR | 2 660 562 | 10/1991 |
| GB | 2 270 264 A | 3/1994 |
| WO | WO 94/21196 | 9/1994 |

OTHER PUBLICATIONS

International Search Report and Written Opinion of the International Searching Authority from corresponding PCT application No. PCT/US2006/006875, Dated Jun. 22, 2006, 10 pages.

* cited by examiner

*Primary Examiner* — Alvin Stewart
*Assistant Examiner* — Yashita Sharma
(74) *Attorney, Agent, or Firm* — Brinks Hofer Gilson & Lione

(57) ABSTRACT

A stent is described that is capable of expanding and thereafter recoiling to its initial coiled state within a biliary duct. A delivery system is utilized to deploy the stent in its natural coiled state into a targeted site of an occluded biliary duct. A balloon from the delivery system is positioned within a lumen defined by the inner coiled arm of the stent. The inflation of a balloon from the delivery system causes the inner coiled arm to radially move outward and engage the outer coiled arm to form an expanded stent. The expanded stent can revert back to its recoiled state by deploying a balloon through a lumen of the expanded stent. Inflation of the balloon disengages the inner coiled arm from the outer coiled arm thereby collapsing the inner coiled arm radially outward and onto the outer coiled arm to form a recoiled stent. The recoiled stent can be removed from the biliary duct.

19 Claims, 5 Drawing Sheets

REMOVABLE COILED STENT

RELATED APPLICATION

This application claims the benefit of priority from U.S. provisional application No. 60/657,544 filed Feb. 28, 2005, which is incorporated herein by reference.

TECHNICAL FIELD

The invention generally relates to balloon-expandable stents, and in particular to removable stents.

BACKGROUND

Stents are frequently used to enlarge, dilate or maintain the patency of narrowed body lumens. A stent may be positioned across a narrowed region while the stent is in a compressed state. The stent may then be expanded in order to widen the lumen. Stents used in the gastrointestinal system are commonly constructed of plastic. Plastic stents facilitate retrieval and/or replacement of the stent during a follow-up procedure. However, plastic stents are not expandable. That is, plastic stents have a fixed diameter. Since plastic stents are frequently delivered through the working channel of an endoscope, the diameter of the working channel limits the diameter of the stent. For example, plastic stents typically have a diameter that is no greater than 11.5 French. However, such a small diameter stent rapidly becomes clogged within the biliary and pancreatic ducts, thereby requiring replacement every three months, or even sooner.

Stents constructed of various metal alloys have also been used within the biliary and pancreatic ducts. These types of metal stents may be self-expanding or balloon expandable, and are designed to expand to a much larger diameter than the plastic stents described above. Consequently, such metal stents remain patent longer than plastic stents, averaging perhaps 6 months before clogging. However, the capability of larger diameter stents to collapse into endoscopic delivery systems necessitates mesh or wire geometries which incur tissue in-growth, thereby rendering the stent permanent and impossible to remove. Therefore, even when a retrievable metal stent has been employed, it may not be possible to remove it without damaging surrounding tissues. Moreover, because these types of stents often comprise nitinol, they tend to expand during deployment. As a consequence, there can be a risk that such a nitinol stent would expand before it is properly deployed in the desired lumen region.

Coiled stents with multiple coils have also been employed. Such stents can undergo the required expansion within a targeted ductal region and remain flexible. However, such stents attain their expanded diameter by undergoing a considerable shortening of their length i.e., foreshortening. Considerable foreshortening results in difficulty deploying the stent at a precise position.

In view of the drawbacks of current stents, an improved stent is needed that is highly compressible, expandable, retrievable, and/or limits or prevents endothialization.

SUMMARY

Accordingly, it is an object of the present invention to provide a stent that resolves or improves upon one or more of the above-described drawbacks.

In a first aspect, a stent is disclosed including an inner coiled arm with an inner end, an outer coiled arm with an outer free-end, and a notch located on the outer free-end. In use, a balloon or expandable device is positioned within a lumen defined by the inner coiled arm. Inflation of the balloon causes the inner coiled arm to uncoil until the inner end of inner coiled arm engages the notch on the outer free-end so as to form an expanded stent.

In a second aspect, an expanded stent is disclosed that is capable of reverting to a recoiled state. In use, a balloon catheter or expanded device is deployed through a lumen of the expanded stent. The balloon or expandable device located on the catheter is inflated thereby forcing the inner coiled arm to radially extend beyond the outer coiled arm, thereby disengaging the inner coiled arm from the outer coiled arm. The balloon or expandable device is then contracted to allow the stent to collapse.

In a third aspect, a stent having controlled expansion is disclosed. A balloon or expandable device is inflated through a lumen of the stent thereby forcing inner coiled arm to uncoil. During the expansion, an inner end of the inner coiled arm engages one of a series of notches to form an expanded stent. The expansion state of the stent at each of the series of notches can be monitored to permit selection of a stent diameter that is best suited for the patient's needs.

BRIEF DESCRIPTION OF THE DRAWINGS

Embodiments of the present invention will now be described by way of example with reference to the accompanying drawings, in which.

DETAILED DESCRIPTION OF THE PREFERRED EMBODIMENTS

Figure 1:
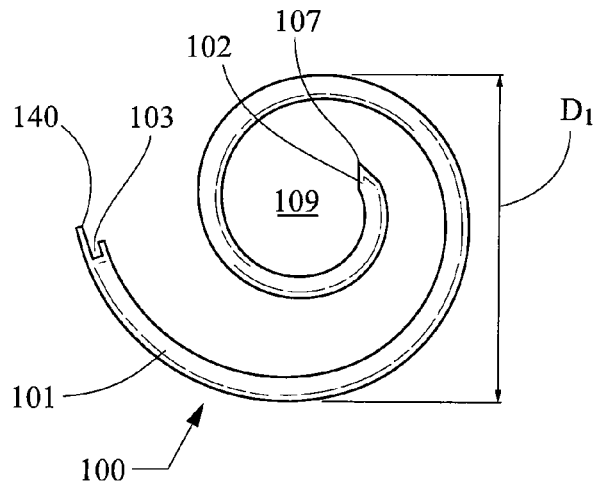
FIG. 1 is a side view of a coiled stent.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly.

Figure 2:
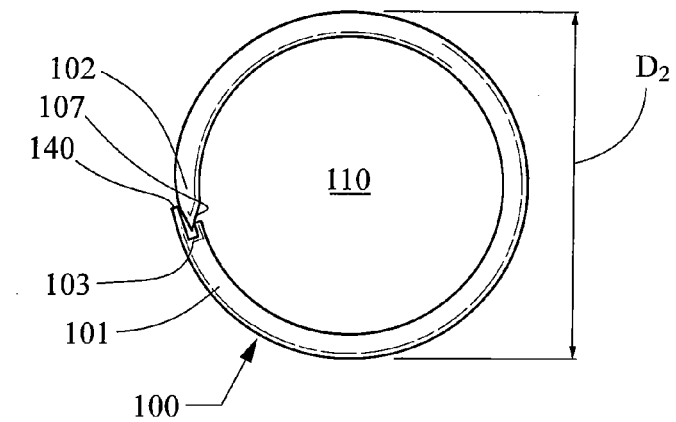
FIG. 2 is a side view of the coiled stent of FIG. 1 in an expanded position.
Figure 3:
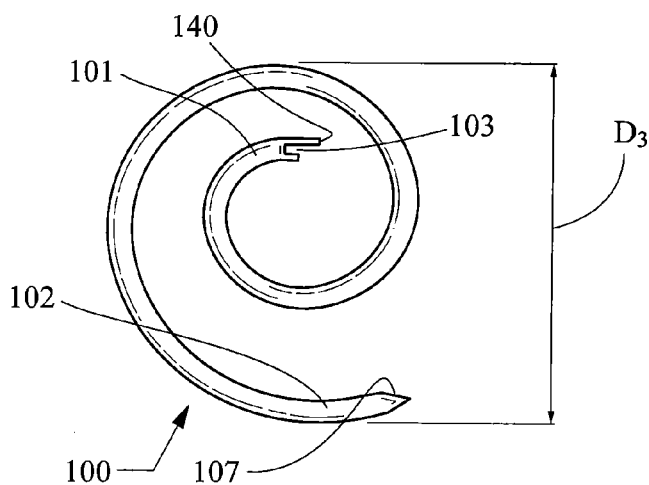
FIG. 3 is a side view of the coiled stent of FIG. 1 in a recoiled position.

FIGS. 1, 2, and 3 show one embodiment of the present invention of a coiled stent 100 that can be delivered endoscopically to a biliary duct. FIG. 1 illustrates the coiled stent 100 in its initial coiled state. Coiled stent 100 includes an inner coiled arm 102, inner end 107 located radially inward of inner coiled arm 102, outer coiled arm 101, and notch 103 located on the outer free-end 140 of outer coiled arm 101. Inner coiled arm 102 is situated radially inward relative to outer coiled arm 101 arm. Coiled stent 100 is biased in this coiled configuration as shown in FIG. 1 until expansion occurs. Coiled stent 100 maintains this initial coiled configuration having an initial diameter $D_1$ in the radial direction prior to expansion. Additionally, the coiled configuration of stent 100 as shown in FIG. 1 renders it highly flexible in such a contracted state. The ability of coiled stent 100 to maintain flexibility in a contracted state facilitates delivery and deployment of coiled stent 100 into the tortuous regions commonly encountered within the biliary duct.

FIG. 2 illustrates stent 100 in an expanded state. Stent 100 is capable of remaining patent within biliary duct 150 for extended periods of time, perhaps indefinitely, thereby facilitating drainage of contents from biliary duct 150. Inner end 107 can be tapered to ensure a secure fit within notch 103. The engagement of notch 103 with inner end 107 ensures that expanded stent 100 is locked in this expansive state. Moreover, the secure engagement of inner end 107 of inner coiled arm 102 with notch 103 of outer coiled arm 101 ensures that expanded stent 100 remains longitudinally and axially stable. Such structural stability eliminates the risk of expanded stent 100 migrating from the targeted occluded biliary duct 150 region.

FIG. 3 shows stent 100 recoiled and collapsed upon itself to a size and shape similar to its initial deployed state. Because stent 100 precludes endothelialization, it is capable of being removed from the biliary duct 150 after a prolonged period of time.

Figure 11:
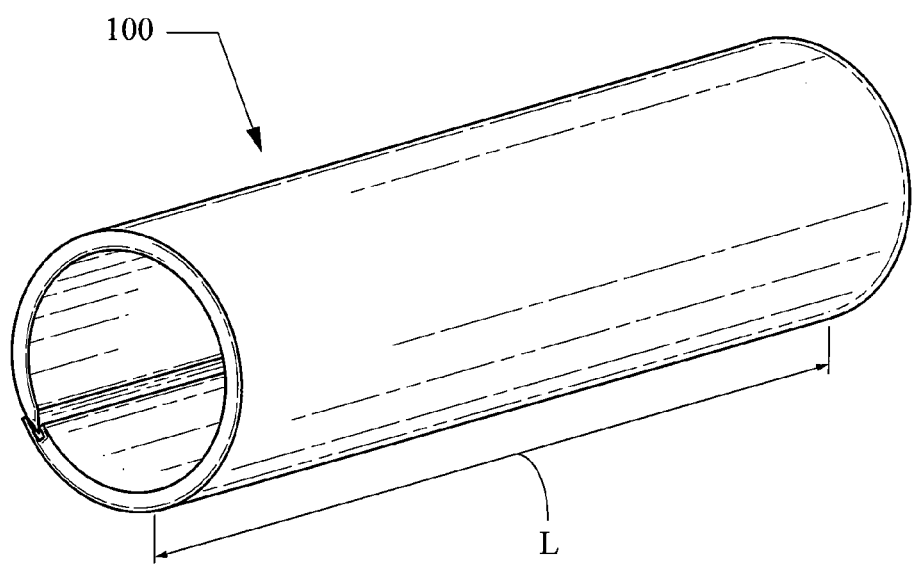
FIG. 11 is a longitudinal end view of a coiled stent.

Diameter $D_1$ of coiled stent 100 as shown in FIG. 1 ranges from about 2 to 3 mm. Such a diameter facilitates loading coiled stent 100 through the working channel of an endoscope. FIG. 1 indicates diameter $D_1$ of coiled stent 100 enables it to slidably fit within a delivery system 121 (shown in FIGS. 4 and 5) such that delivery system 121 can fit within an endoscopic working channel. Expanded diameter $D_2$ can range from about 8 to 14 mm depending on the intended use for the stent. Expanded stent 100, as shown in FIG. 2, can expand up to 7 times the original coiled diameter $D_1$ of coiled stent 100, shown in FIG. 1, while maintaining its structural integrity in the expanded state. FIG. 11 illustrates a length L of coiled stent 100 that ranges from about 4-12 cm, although shorter or larger stents can be employed.

Figure 6:
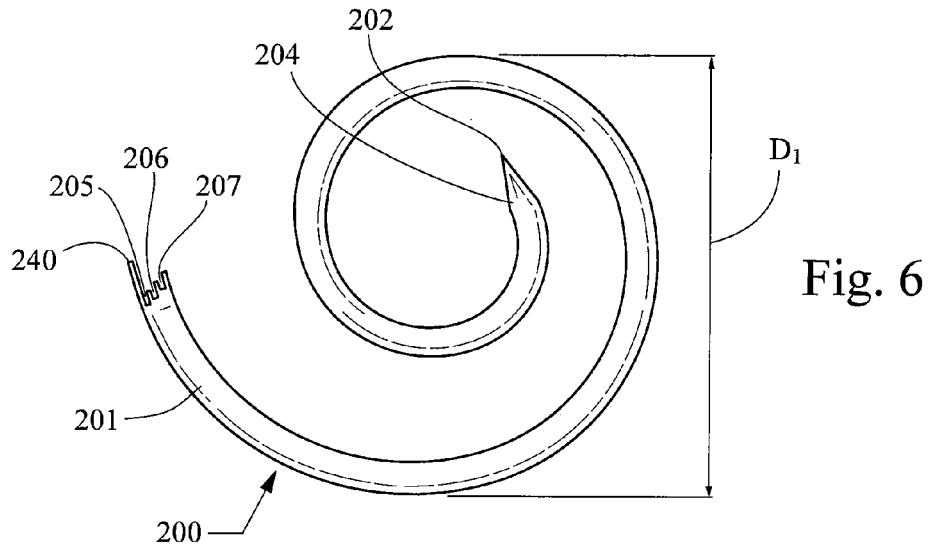
FIG. 6 is a side view of a coiled stent in an initial coiled state having three notches.
Figure 7:
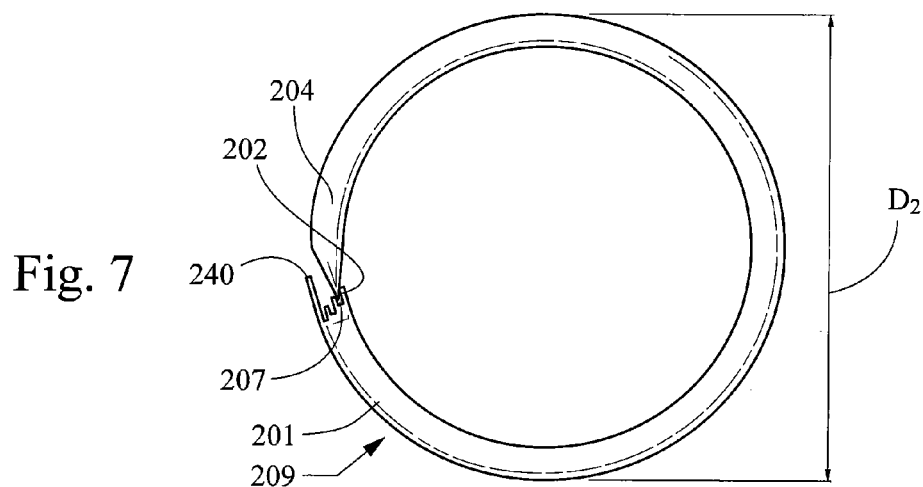
FIG. 7 is a side view of the coiled stent in a first expanded state.
Figure 8:
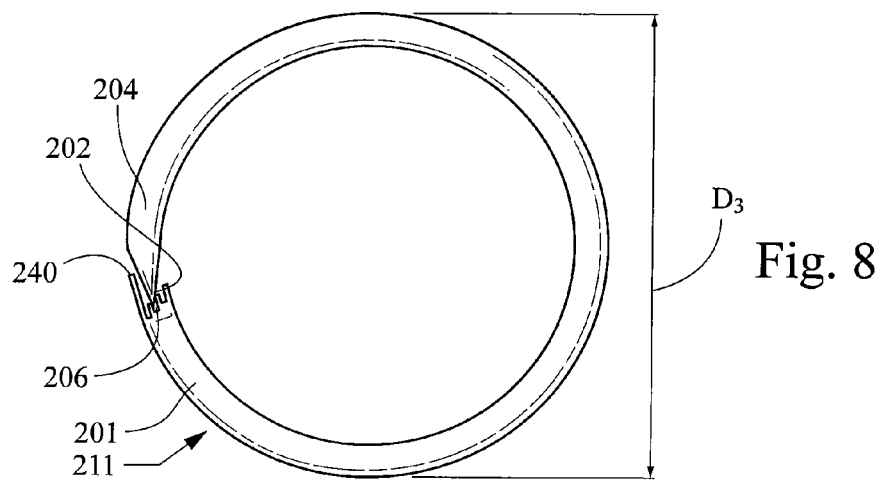
FIG. 8 is a side view of the coiled stent of FIG. 6 in a second expanded state.

A stent can also include multiple notches. FIGS. 6, 7, and 8 illustrate a stent 200 that has the capability to selectively expand to a range of diameters. In particular, outer coiled arm 201 is provided with a plurality of notches situated along the outer free-end 240 of outer coiled arm 201. For example, FIGS. 6, 7, and 8 show a stent 200 having three notches, 205, 206, and 207, situated along the outer free-end 240 of outer coiled arm 201. Notches 205, 206, and 207 permit initially coiled stent 200 to be expanded to three different diameters.

A surgeon can select the desired notch of expansion by visualization of the expanded balloon 120 (FIG. 5), the expanded stent, or a combination of both. Radiopaque fluids and inks that are commonly known to those skilled in the art can be used to inflate balloon 120. Visualization of the incremental inflation of balloon 120 can indicate the degree of expansion stent 200 is undergoing. Echogenicity can also be incorporated onto the surfaces of inner coiled arm 204 and outer coiled arm 201 to provide ultrasound visualization of the expanding stent 200. A specific example of creating echogenicity is described in U.S. Pat. No. 4,869,259 issued to Elkins, which is incorporated in its entirety herein by reference.

FIGS. 6, 7, and 8 illustrate that notches 205, 206, and 207 are downwardly sloped as stent 200 radially expands. Such a downward slope orientation ensures that inner coiled arm 204 can only travel radially outward, thereby preventing reversion of stent 200 back to its first biased coiled state as shown in FIG. 6. Nevertheless, the angle of notches 205, 206, and 207 should be sufficiently acute to ensure that inner coiled arm 204 will not inadvertently slip to the next outwardly radially located notch, thereby preventing inadvertent expansion of stent 200 to the next larger state.

Such a ratcheted mechanism on outer coiled arm 201, as shown in FIGS. 6, 7, and 8 enables stent 200 to conform to the specific contours of the targeted site in biliary duct 150 in a particular patient and thereby adapt to different-sized biliary tracts. Additionally, notches 205, 206, and 207 in conjunction with the above described visualization techniques allow stent 200 to be expanded in a controlled incremental manner.

Coiled stent 100 is preferably formed from any conventional metal or metal alloy capable of remaining coiled in the absence of any compressive or tensile forces. Other materials, however, may also be employed such as plastic.

Figure 9:
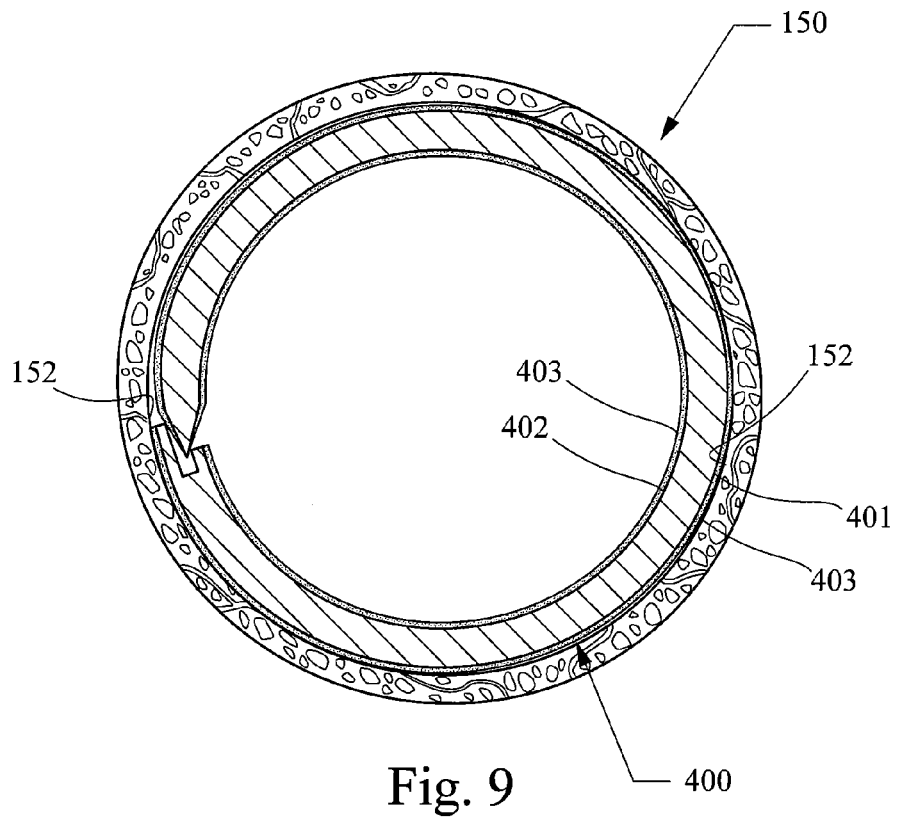
FIG. 9 is a partial cross-sectional view of an expanded stent within a target site of a biliary duct having a polymer coating.

In accordance with another embodiment of the present invention, the surfaces of the stent can be coated with a polymer. FIG. 9 illustrates balloon-expanded stent 400 deployed in biliary duct 152 having a polymer coating 403 on both its outer surface 401 and its inner surface 402. The polymer coating 403 on outer surface 401 and inner surface 402 can be a biocompatible polymer. The polymer coating 403 can also be with a PTFE coating. Polymer coating 403 can also comprise a hydrophilic polymer selected from the group comprising polyacrylate, copolymers comprising acrylic acid, polymethacrylate, polyacrylamide, poly(vinyl alcohol), poly(ethylene oxide), poly(ethylene imine), carboxymethylcellulose, methylcellulose, poly(acrylamide sulphonic acid), polyacrylonitrile, poly(vinyl pyrrolidone), agar, dextran, dextrin, carrageenan, xanthan, and guar. The hydrophilic polymers can also include ionizable groups such as acid groups, e.g., carboxylic, sulphonic or nitric groups. The hydrophilic polymers may be cross-linked through a suitable cross-binding compound. The cross-binder actually-used depends on the polymer system: If the polymer system is polymerized as a free radical polymerization, a preferred cross-binder comprises 2 or 3 unsaturated double bonds.

The polymer coating 403 on inner surface 402 and outer surface 401 of expanded stent 400 can also be loaded with a variety of bioactives. The polymer coating 403 is capable of releasing the bioactive into the body at a predetermined time and at a predetermined rate. Such polymeric coatings 403 include drug-eluting matrix materials described in U.S. Pat. Nos. 5,380,299, 6,530,951, 6,774,278 and U.S. patent application Ser. Nos. 10/218,305, 10/223,415, 10/410,587, 10/000,659, and 10/618,977 which are incorporated in their entirety herein by reference.

Figure 10:
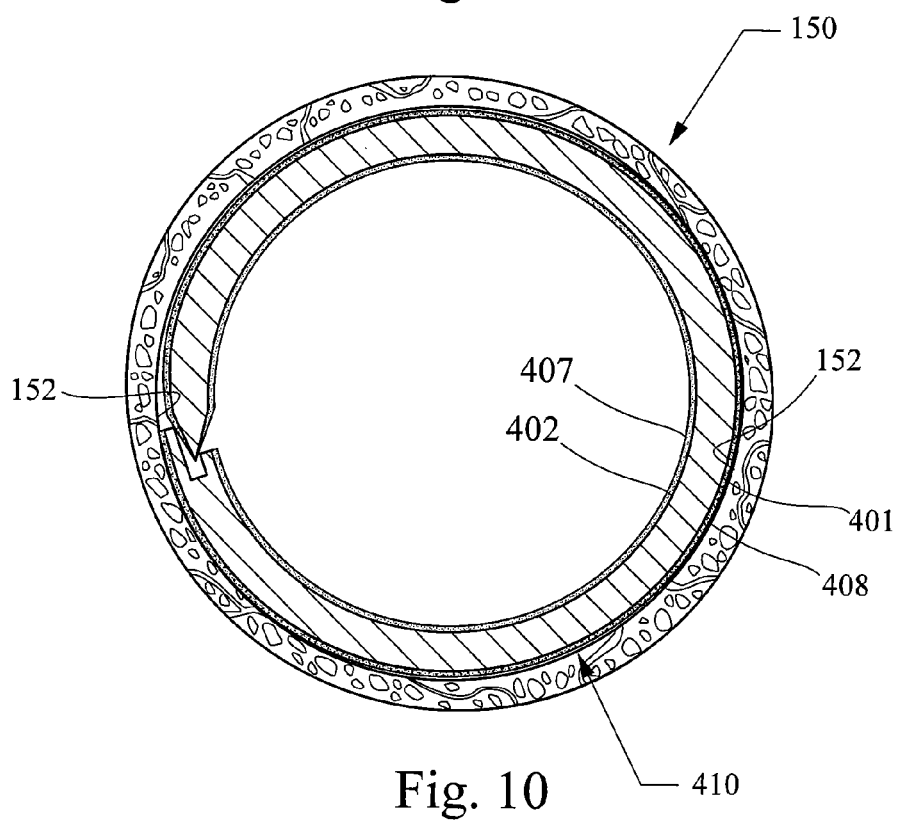
FIG. 10 is a partial cross-sectional view of an expanded stent having a first polymer coated outer surface and a second polymer coated inner surface.

Alternatively, FIG. 10 indicates that different polymer coatings can be coated on outer surface 401 and inner surface 402 of expanded stent 410. For example, the polymer coating 408 on outer surface 401 includes any polymer coating commonly known to those skilled in the art to help reduce tissue irritation incurred as a result of expanded stent 410 being in contact with inner wall 152 of biliary duct 150 for a prolonged period of time. The polymer coating 407 on inner surface 402 includes any coating commonly known to those skilled in the art to prevent undesirable deposition of inner surface 402, which can ultimately cause clogging of expanded stent 410.

Alternatively, inner coiled arm 102 and outer coiled arm 101 of expanded stent 100 (FIG. 2) can be composed from a rigid dissolvable polymer that gradually bioerodes with time. Rigid dissolvable polymers include poly(lactid acid), poly (glycolic acid), and poly-epsilon-capro-lactone, or combinations thereof. Other rigid dissolvable polymers will be apparent to those of ordinary skill in the art.

Figure 4:
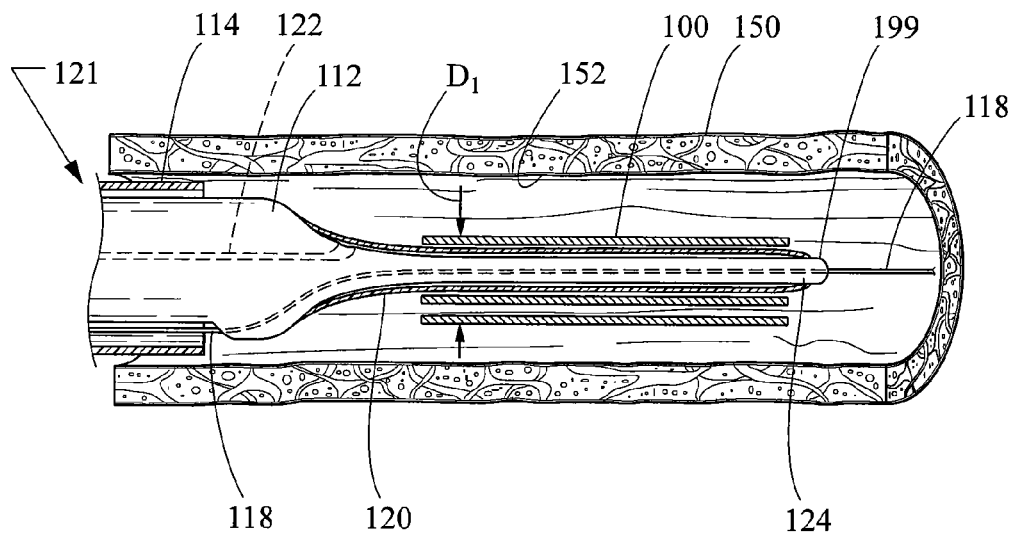
FIG. 4 is a partial cross-sectional view of a delivery system used to deploy a coiled stent.
Figure 5:
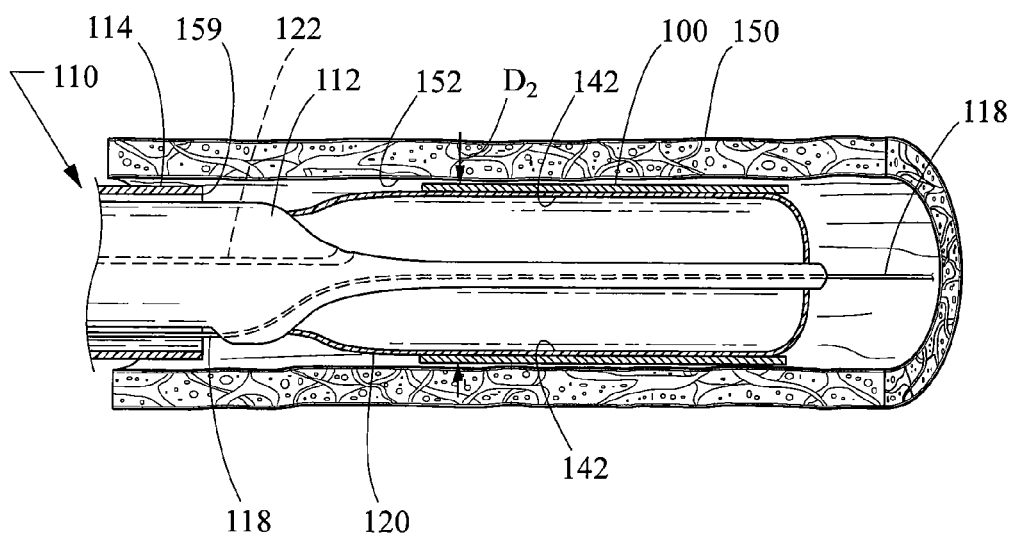
FIG. 5 is a partial cross-sectional view of a delivery system expanding a stent at the target site within biliary duct.

FIGS. 4 and 5 show a delivery system 121 used to deploy stent 100 within the biliary duct 150. The delivery system 121 has an outer catheter 114 and a balloon catheter 112. The balloon catheter 112 is coaxially disposed within outer catheter 114. The balloon catheter 112 includes a balloon 120 attached to an inflation lumen 122 that extends through the catheter 112 and is connected to a source for an inflation fluid. A guidewire lumen 124 extends through the distal portion of the catheter 112 and the balloon 120. Guidewire lumen 124 enables balloon catheter 112 to be passed over the guidewire 118 which is used to guide the balloon catheter 112 to the target site. To minimize frictional resistance between the interior of the passage and the surface of the guidewire 118, the inside of the passage and/or the top of the guidewire 118 may be provided with a lubricant coating. Depending on the size of the stent and the procedure to be carried out, the balloon 120 is between about 5 and 100 mm in length, and the inflation lumen 122 is between about 100 and 1500 mm in length. However, a wider variety of balloon and catheter lengths for use in different procedures will become apparent to one of ordinary skill in the art in view of the present disclosure. An exemplary type of balloon catheter 112 is described in U.S. Patent Application Ser. No. 60/651,028, "SELF CONTRACTING STENT", which is incorporated herein by reference. It should be understood that other types of expandable devices, other than balloons, could be employed to deliver and deploy stent 100.

A procedure for deploying the stent is now described. FIG. 4 shows coiled stent 100 mounted on balloon 120. Inner coiled arm 102 and outer coiled arm 101 of coiled stent 100 (FIG. 1) are tightly wound around balloon 120. Coiled stent 100 is secured between outer catheter 114 and balloon 120 such that coiled stent 100 remains in place on balloon 120 during delivery into the biliary duct 150. During deployment, outer catheter 114 extends longitudinally to the distal end 199 of delivery system 121 thereby covering stent 100.

In use, an endoscope (not shown) is first positioned at the desired region within the duoedenum. Guidewire 118 is then deployed through the working channel of the endoscope and guided through the papilla and into the desired region of the biliary duct 150. Delivery system 121 is thereafter loaded coaxially onto guidewire 118, as shown in FIG. 4. During insertion of delivery system 121, only the exterior surface of the outer catheter 114 is in contact with the walls of the endoscope and body lumen.

Once delivery system 121 is positioned adjacent the desired region within the biliary duct 150, coiled stent 100 is ready to be deployed from delivery system 121. Balloon 120 extends from both ends to an active region 142 around which the stent 100 is mounted to, as illustrated in FIGS. 4 and 5. The active region 142 is the region of the balloon 120 which expands the stent 100 against an inner wall 152 of the biliary duct 150, as illustrated in FIG. 5. Deployment is shown in FIG. 5. Deployment of coiled stent 100 requires that the entire longitudinal length of balloon catheter 112 be exposed within the biliary duct 150. This is accomplished by either retracting the distal end 159 of outer catheter 114 or advancing the balloon catheter 112 distally of the distal end 159 of outer catheter. Either method will produce an entirely exposed coiled stent 100, as shown in FIG. 5. With the distal end 159 of outer catheter 114 now positioned proximal to coiled stent 100 and balloon catheter 112 balloon 120 can undergo expansion. As balloon 120 is inflated, coiled stent 100 expands at desired biliary duct region 150. In particular, inflation of balloon 120 causes coiled stent 100 to expand along its entire length.

During expansion of stent 100, the inner coiled arm 102 and outer coiled arm 101 expand radially outward (FIGS. 2 and 5). Inner end 107 and notch 103 will slide in a circumferential direction with respect to one another. Inner end 107 of inner coiled arm 102 engages with notch 103, such that an expanded stent 100 (FIGS. 2 and 5) having a circular shape is formed. Inner end 107 is tapered to ensure a secure fit within notch 103 (FIG. 2).

Stent 200 of FIG. 6 can also be delivered and deployed using delivery system 121. Inflation of balloon 120 will cause inner end 202 and notch 207 to slide in a circumferential direction with respect to one another until inner end 202 and notch 207 engage to form a first expansion state 209 as shown in FIG. 7. Stent 209 can be incrementally expanded to a second expansion state 211, as shown in FIG. 8, if so desired. Alternatively, after inner wall 152 of biliary duct 150 has potentially enlarged in response to pressure exerted by stent 209 over a period of time, a surgeon can reenter biliary duct 150 and expand stent 209 to the second expansion state of stent 211 corresponding to notch 206 of FIG. 8. Thus, use of stent 200 having a plurality of notches enables a technique for gradually dilating a lumen without having to introduce a larger stent during each subsequent incremental expansion.

After deploying the expanded stent 100, the balloon 120 is then deflated and balloon catheter 112 is completely inserted back into the distal end 159 of outer catheter 114, leaving the expanded stent 104 within biliary duct 150, as shown in FIG. 5.

As illustrated in FIG. 3, stent 100 can be collapsed after it is expanded. This may be necessary in order to withdraw or reposition the stent. In order to collapse stent 100 of FIG. 2, a catheter is inflated within lumen 110. As the balloon inflates, inner coiled arm 102 moves radially outward beyond notch 103, thereby disengaging inner coiled arm 102 from notch 103. Upon disengagement, inner coiled arm 102 collapses radially outward and onto outer coiled arm 101 thereby resuming a coiled configuration, as illustrated in FIG. 3.

Recoiled stent 100 assumes a diameter $D_3$ (FIG. 3). The ability to have the radial dimension of recoiled stent 100 return to its initial state enables it to be removed from biliary duct 150. Recoiled stent 100 having recoiled diameter $D_3$ can be withdrawn from biliary duct 150 through an overtube by the use of forceps or other similar endoscopic devices.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. For example, the invention has been described in the context of accessing the biliary duct. Application of the principles of the invention to access other body cavities, such as the pancreatic duct and thoracic cavity, by way of a non-limiting example, are within the ordinary skill in the art and are intended to be encompassed within the scope of the attached claims. Moreover, in view of the present disclosure, a wide variety of expandable stents and methods of their uses will become apparent to one of ordinary skill in the art.

The invention claimed is:

1. A stent consisting essentially of:
a coil having a first edge formed by a first free end of a first coiled arm and a second edge formed by a second free end of a second coiled arm, and a curvilinear axis extending circumferentially between the first free end and the second free end;
a single pointed tip formed at the second free end of the second edge and having opposing smooth tapered surfaces; and
a plurality of notches positioned at the first free end of the first edge, the plurality of notches being disposed in a plane transverse to the curvilinear axis, each of the plurality of notches being defined by a pair of spaced apart walls configured to receive the pointed tip of the second free end there between,
wherein the plurality of notches are oriented along a downward slope so as to form a stepped configuration.

2. The stent of claim 1 having a first configuration wherein the second edge is situated radially inward of the first edge when the stent is in a first state.

3. The stent of claim 2 having a second configuration wherein the second free end of the second edge is engaged with at least one of the plurality of notches when the stent is in a second state, the second state being relatively more expanded than the first state.

4. The stent of claim 3 having a third configuration wherein the second edge is situated radially outward of the first edge.

5. The stent of claim 1 wherein the stent is formed from a metal.

6. The stent of claim 5 wherein the metal is selected from the group consisting of stainless steel, cobalt chromium alloy, and nitinol.

7. The stent of claim 1 wherein the stent is formed from a rigid plastic.

8. The stent of claim 1 wherein the stent is formed from a bioerodible plastic.

9. The stent of claim 8, wherein the bioerodible plastic is selected from the group consisting of poly(lactid acid), poly(glycolic acid), and poly-epsilon-capro-lactone.

10. The stent of claim 1 wherein a first surface of the coil is coated with a first polymer.

11. The stent of claim 10 wherein a second surface of the coil is coated with a second polymer.

12. The stent of claim 10 wherein the first polymer is a drug-eluting polymeric carrier.

13. The stent of claim 11 wherein the second polymer is a drug-eluting polymeric carrier.

14. The stent of claim 1 wherein at least one of the first edge and second edge comprises radiopaque markers for visualization.

15. The stent of claim 1 wherein at least one of the first edge and second edge comprises echogenic markers for visualization.

16. The stent of claim 1 wherein the coil defines an interior lumen having a longitudinal axis, and further wherein the plurality of notches each extend substantially parallel to the longitudinal axis.

17. The stent of claim 1 wherein the second edge is configured to engage any one of the plurality of notches.

18. The stent of claim 17, wherein the engagement of the second edge with any one of the plurality of notches is designed to be adjustable.

19. A stent consisting essentially of
a coil having a first edge formed by a first free end of a first coiled arm and a second edge formed by a second free end of a second coiled arm, wherein the first edge is separated from the second edge by a curvilinear axis extending circumferentially therebetween and defining an interior area of the coil;
a single outwardly projecting male engagement member formed at the second free end of the second edge and having opposing smooth tapered surfaces; and
a plurality of inwardly projecting female engagement notches positioned at the first free end of the first edge, each of the plurality of female engagement notches being configured to receive the single male engagement member of the second free end of the second edge such that the second free end is substantially disposed between an inner and an outer surface of the first free end,
wherein the plurality of female engagement notches are oriented along a downward slope so as to form a stepped configuration, and
wherein the plurality of notches are disposed along a single plane that extends transverse to the interior area of the coil.

* * * * *